United States Patent
Oliva

(10) Patent No.: US 7,461,653 B2
(45) Date of Patent: Dec. 9, 2008

(54) SINGLE DOSE INHALER

(76) Inventor: Roberto Oliva, Via Mar di Barents, 2-41012 Carpi (IT)

( * ) Notice: Subject to any disclaimer, the term of this patent is extended or adjusted under 35 U.S.C. 154(b) by 448 days.

(21) Appl. No.: 10/530,966

(22) PCT Filed: Oct. 13, 2003

(86) PCT No.: PCT/IT03/00617

§ 371 (c)(1),
(2), (4) Date: Apr. 11, 2005

(87) PCT Pub. No.: WO2004/035121

PCT Pub. Date: Apr. 29, 2004

(65) Prior Publication Data

US 2006/0060194 A1    Mar. 23, 2006

(30) Foreign Application Priority Data

Oct. 16, 2002    (IT) .......................... MO2002A0297

(51) Int. Cl.
- A61M 15/00  (2006.01)
- A61M 16/00  (2006.01)
- B05D 7/14   (2006.01)
- B65D 83/06  (2006.01)

(52) U.S. Cl. .............................. 128/203.21; 128/203.15

(58) Field of Classification Search ............ 128/203.12, 128/203.15, 203.18, 203.19, 203.21, 200.24, 128/203.23, 205.21

See application file for complete search history.

(56) References Cited

U.S. PATENT DOCUMENTS

| | | | | |
|---|---|---|---|---|
| 2,587,215 A * | 2/1952 | Priestly | ................. | 128/203.15 |
| 4,013,075 A * | 3/1977 | Cocozza | ................. | 128/203.15 |
| 4,064,878 A * | 12/1977 | Lundquist | .............. | 128/203.15 |
| 4,117,844 A * | 10/1978 | James | .................... | 128/203.15 |
| 4,206,758 A * | 6/1980 | Hallworth et al. | ...... | 128/203.15 |
| 4,227,522 A * | 10/1980 | Carris | ................... | 128/203.15 |
| 4,846,168 A * | 7/1989 | Abiko et al. | ........... | 128/203.15 |
| 4,860,740 A * | 8/1989 | Kirk et al. | .............. | 128/203.15 |
| 5,651,359 A * | 7/1997 | Bougamont et al. | .... | 128/203.15 |
| 5,673,686 A * | 10/1997 | Villax et al. | ........... | 128/203.15 |
| 6,470,884 B2 * | 10/2002 | Horlin | ................... | 128/203.15 |
| 7,025,059 B2 * | 4/2006 | Pera | ..................... | 128/203.21 |
| 2005/0115563 A1 * | 6/2005 | Pera | ...................... | 128/203.15 |

FOREIGN PATENT DOCUMENTS

| DE | 196 37 125 | 3/1998 |
| EP | 1 238 680 | 9/2002 |
| WO | 97 27892 | 8/1997 |
| WO | 01 87393 | 11/2001 |

* cited by examiner

Primary Examiner—Justine R. Yu
Assistant Examiner—Kristen C Matter
(74) Attorney, Agent, or Firm—Browdy and Neimark, P.L.L.C.

(57) ABSTRACT

An inhalator composed of a main body affording an inhalation conduit; a second body exhibiting a housing, into which a capsule can be at least partially inserted; the second body being rotatably coupled with the main body, and being able to rotate from an open position, in which the housing is accessible from outside for insertion of a capsule, and a closed position, in which the housing is in communication with the inhalation conduit; means for cutting off a portion of a capsule which projects from the housing during rotation of the second body from the open position to the closed position.

7 Claims, 3 Drawing Sheets

US 7,461,653 B2

SINGLE DOSE INHALER

TECHNICAL FIELD

The invention relates to an inhalator for single-dose mixtures in capsules. In particular, the inhalator enables inhalation of a mixture, typically powder, closed internally of a capsule made of plastic material which is wholly inserted into the inhalator.

BACKGROUND ART

Inhalators of this type are known in the prior art and are constituted by a container comprising an inhalation conduit in communication with a chamber for housing a capsule containing a pharmaceutical substance to be inhaled. The housing chamber is elongate, and of a same shape as usual capsules for powder-form drugs, and is transversaly arranged with respect to a longitudinal development of the inhalation conduit. Means for breaking open the capsule are associated to the housing chamber and arranged at ends thereof, the means for breaking are constituted by two piercing devices, including a number of sharp teeth which penetrate the housing chamber. The teeth are kept in an external position in relation to the chamber by a plurality of springs and exhibit a portion which is external to the container in which it is possible to exert a pressure with the fingers to cause perforation of the capsule. The powder can at this point exit from the capsule and be inhaled.

EP 1 238 680 discloses an inhaler comprising: means to hold the capsule inside said cover, with an open compartment, of circular shape, placed directly inside the cover, into which the capsule is placed, resting on the circular groove of said compartment; means to hold the pieces of the case of the capsule, after it has been split, and to prevent the powder from aggregating, with a reservoir having a series of slots on its walls that hold the bigger pieces inside, while letting the powder pass through; means to close the container, with a cover, which holds the capsule and closes the horizontal chamber, having two outer protrusions on its walls that stop under the inner protrusions of the chamber, preventing the cover from accidentally escaping from its place; means to allow the cover to rotate, thanks to the circular shape of the same cover and the chamber, so as to split the capsule with a simple rotation of the cover, in any direction, till a blade element reaches and cuts the capsule; means to split the capsule, with an element, consisting of a circular plate comprising a hole, whose vertical axis is laterally moved from the one of the inhaler, which holds the lower part of the capsule, so that, by rotating said element, the blade below cuts the lower part of the capsule.

The known-type inhalators exhibit numerous drawbacks,

A main drawback is the presence of a relatively high number of components, considering the presence of the piercing devices, the springs and the maneuvering ends of the piercing devices. Some of these components are in relative motion with respect to the container and there is therefore a liability of malfunctioning or jamming. These components also require careful assembly operations in order to function correctly, which lead to an increase in cost of the inhalator.

Prior art inhalators also exhibit some functional defects. Firstly, perforation of the capsule does not guarantee complete exit of the medicinal substance, as the openings created are at ends of the capsule and small in size. To favour exit of the substance the inhalator has to be shaken and several inhalations performed, and still without the certainty of hag consumed all of the capsule's contents. The position of the housing chamber, which is aligned with the inhalation conduit, is such that the passage of the medicinal substance from the chamber to the inhalation conduit is considerably obstructed. To favour inhalation the device has to be inclined in order to raise the inhalation chamber, and consequently the medicinal substance is not directly aspirated into the trachea but enters partly into contact with the inside of the mouth and is thus less effectively absorbed by the patient.

A further drawback of the inhalators of known type is that the cut portion of the capsule falls into the reservoir together with the powder. A part of the powder may remain entrapped in this cut portion of the capsule, or the cut portion may lay into the reservoir obstructing the flow of the powder through the inhaler, in both cases causing au incomplete inhalation of the powder The main aim of the present invention is to obviate the above-described drawbacks by providing an inhalator for single-dose mixtures in capsules, which is characterized by having a limited number of components.

A further aim of the resent invention is to provide an inhalator in which the medicinal mixture is made available for inhalation by being completely transferred to the inhalation conduit.

A further aim of the present invention is to provide an inhalator in which the mixture is inhaled by means of a simple drawing-in of breath by the user.

DISCLOSURE OF INVENTION

Further characteristic and advantages of the present invention will bear emerge from the detailed description that follows of an inhalator for single-dose mixtures in capsules, in a preferred but non-exclusive embodiment of the invention, illustrated purely by way of non-limiting example in the accompanying figures of the drawings, in which.

Figure 1:
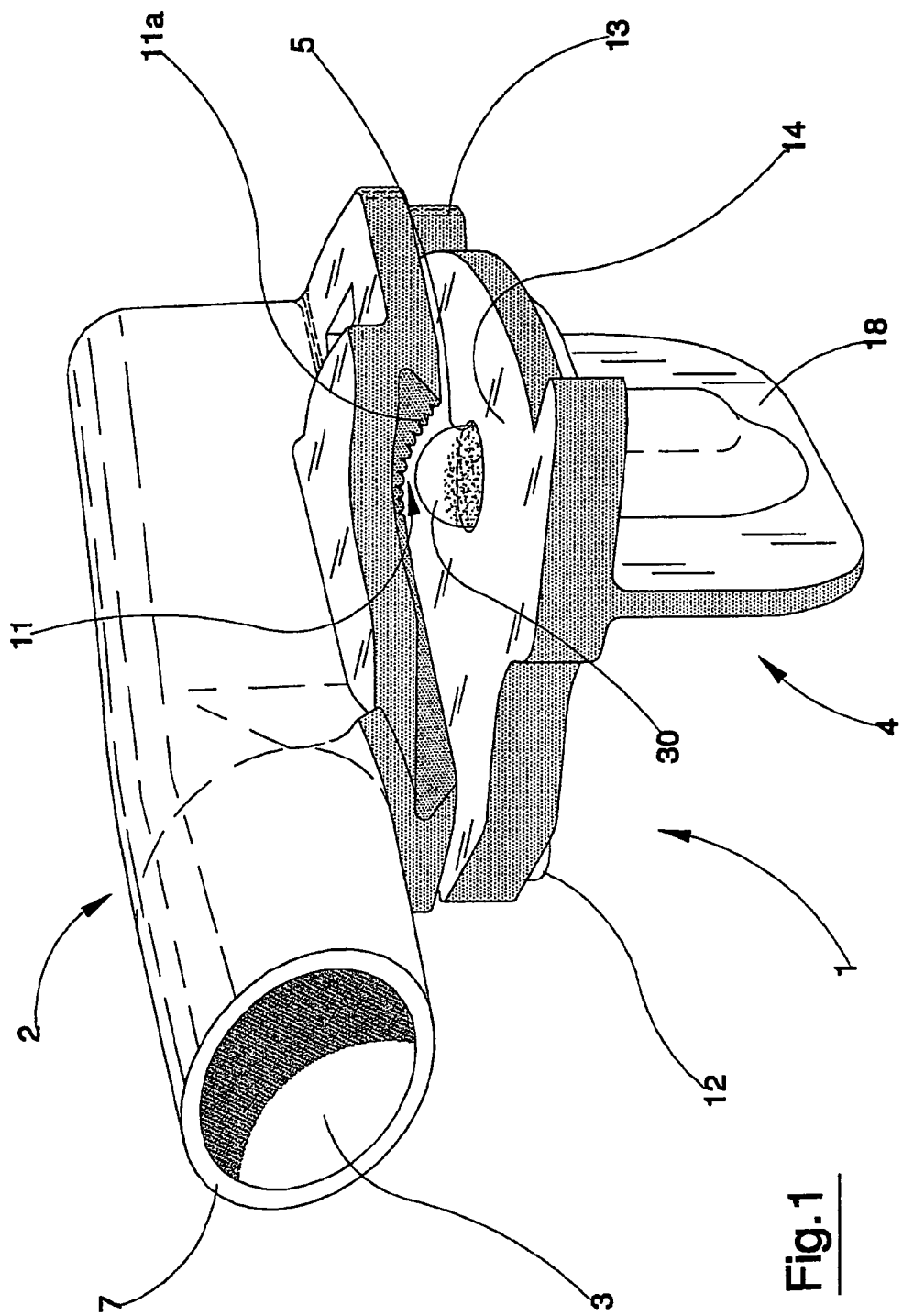
FIG. 1 is a perspective view of an embodiment of the inhalator of the invention, in a first operating configuration.
Figure 2:
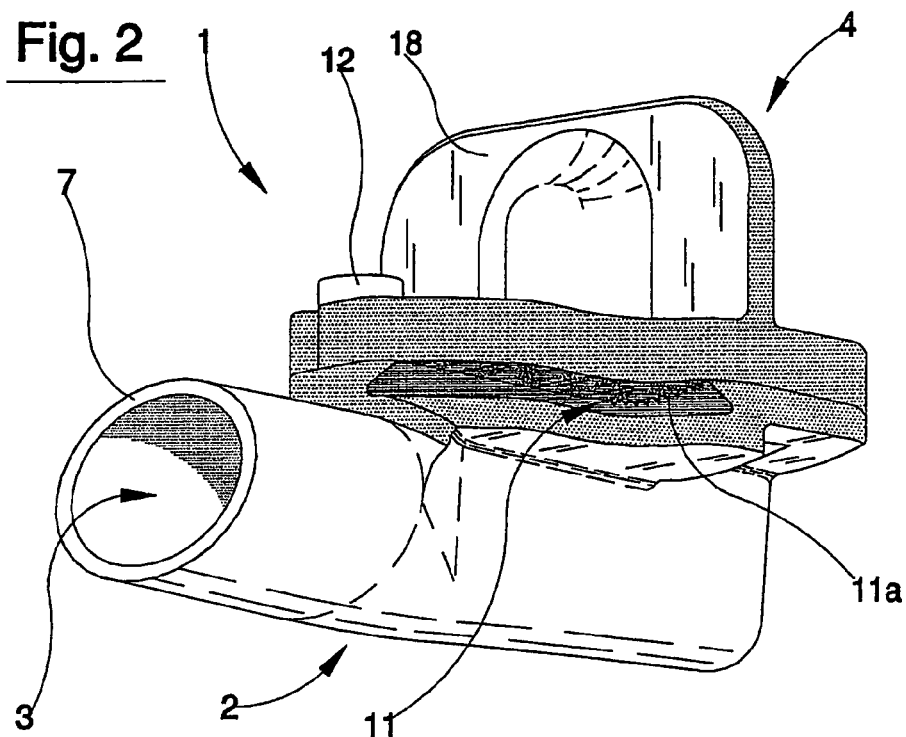
FIG. 2 is a perspective view of the inhalator of FIG. 1 in a second operating configuration.
Figure 3:
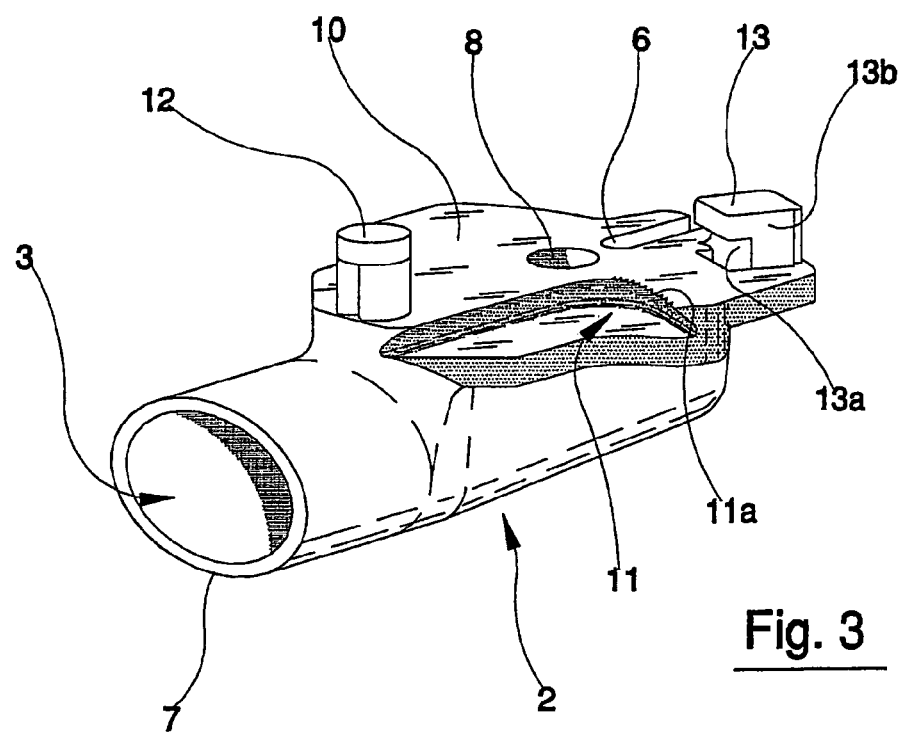
FIG. 3 is a perspective view of a first component of the inhalator of FIG. 1.
Figure 4:
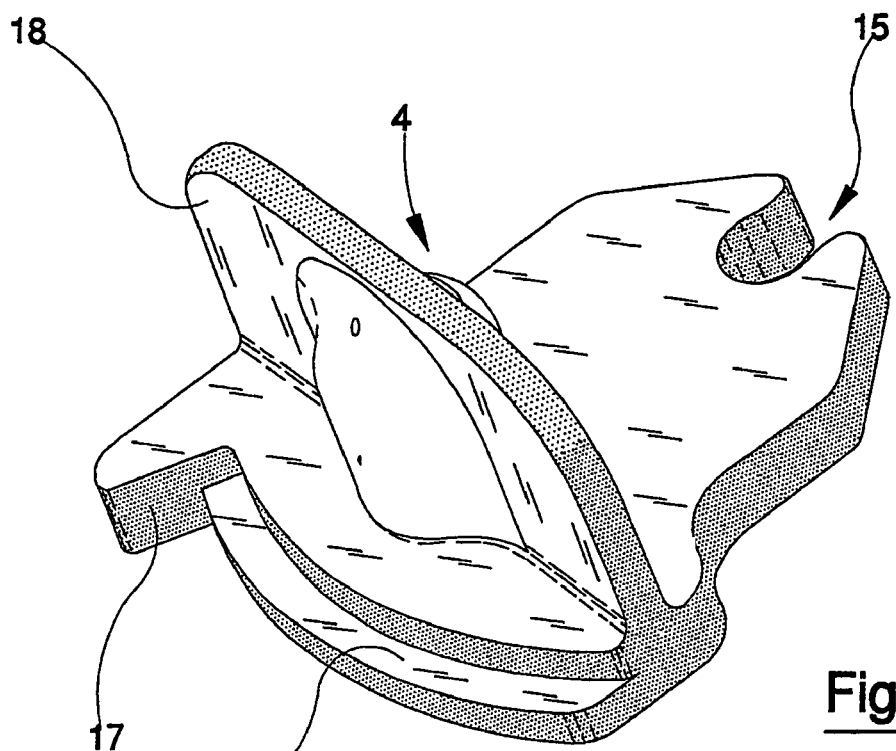
FIG. 4 is a perspective view of a second component of the inhalator of FIG. 1.
Figure 5:
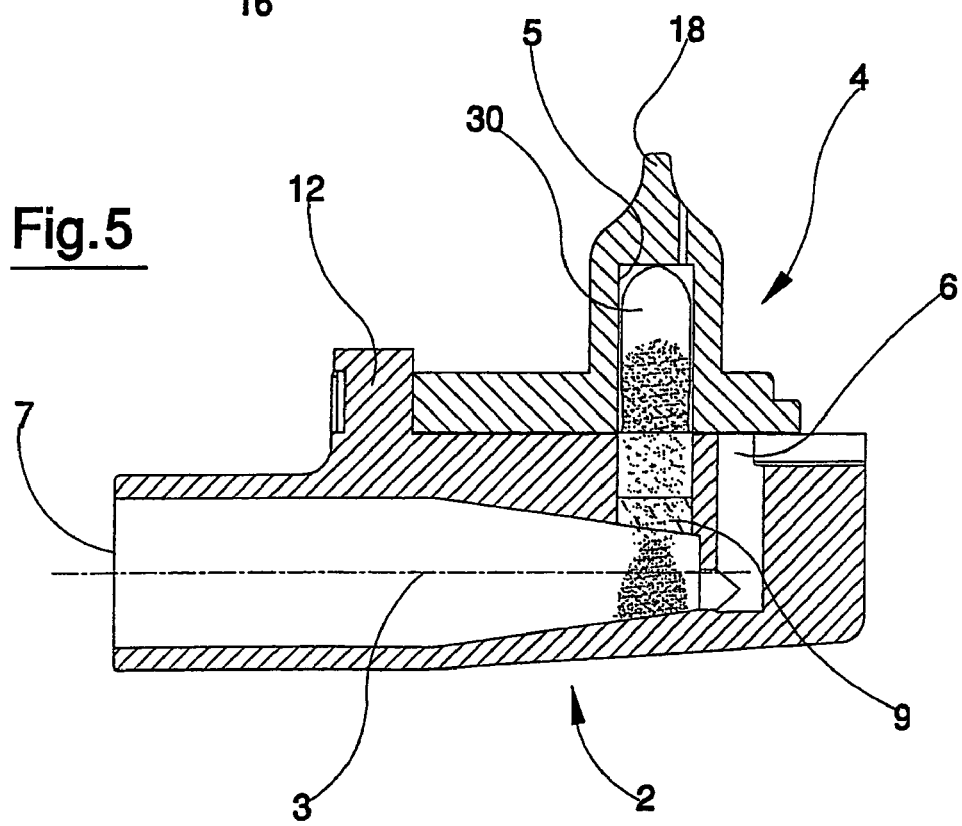
FIG. 5 is a view in section of the inhalator of FIG. 2.

With reference to the figures of the drawings, 1 denotes in its entirety the inhalator of the invention. It comprises a main body 2 having an inhalation conduit 3. The main body 2 comprises a first surface 10 which extends more-or-less planarly and parallel to the longitudinal axis of the inhalation conduit 3 and exhibits a hole 8 for communication with the inhalation conduit 3.

Advantageously the main body 2 can be made of a transparent material.

The inhalator 1 further comprises a second body 4 which exhibits a second surface 14 which is complementarily shaped with respect to the first surface 10 and is in contact there-with. A housing 5 is afforded in the second surface 14, in which a capsule 30 can be at least partially inserted. The second body 4 is rotatably coupled to the main body 2 so that it can rotate from an open position, in which the housing 5 is accessible from the outside for insertion of a capsule 30, to a closed position, in which the housing 5 is aligned with the hole 8.

Advantageously, the second body 4 can be made of a transparent material.

The inhalator 1 further comprises means for cutting 11 for cutting away, as will be better explained herein below, a portion of the capsule 30 which projects from the housing 5 during rotation of the second body 4 from the open position to the closed position.

The first surface 10 is, overall, shaped as a segment of a circle with an apex thereof located in an intermediate position with respect to the longitudinal development of the inhalation conduit 3. The first surface 10 comprises a pivot 12 which is perpendicular to the first surface 10 and is arranged in about the same position as the apex of the first surface 10; the first surface 10 exhibits a guide spur 13 which is perpendicular to the first surface 10 and has a lateral projection 13a and a strike surface 13b. The lateral projection 13a is an undercut afforded on a lateral surface of the spur 13 so that the portion of pivot 12 which is close to the first surface 10 has a smaller section than the remaining portion of the pivot 12.

The means for cutting 11 comprise a cutting edge 11a, arranged peripherally on the first surface 10, which exhibits a sawtooth shape. As the first surface 10 and the second surface 14 are in contact, during the rotation of the second body 4 from the open position to the closed position the portion of the capsule 30 projecting from the housing 5 interferes with the cutting edge 11a, and is cut by the sawtooth edge of the cutting edge. The cut portion remains external of the inhalator.

The inhalation conduit 3 exhibits a first opening 6 for aspiration of air from the outside, arranged on the first surface 10, and a second mouth 7 for inhalation of a single-dose mixture. The hole 8 is arranged on the first surface 10 in an intermediate position between the first and the second mouths 6 and 7. The second mouth 7 is used by the user to aspirate the medicinal mixture, while air passes through the first mouth 6 to enter the inhalator. To facilitate inlet of air through the first mouth 6, a channel can be afforded on the first surface 10, extending from the edge of the first surface 10 to the first mouth 6. In a correct use of the inhalator, once the capsule 30 has been cut, the inhalator is gripped in such a way that the housing 5 is vertical and the cut end of the capsule 30 is facing downwards. The medicinal mixture falls from the capsule 30 into the inhalation conduit through the hole 8 and into the flow of air which is taken in through the first mouth 6 and entrained towards the second mouth 7 by the inhaling action exerted by the user.

The inhalation conduit 3 exhibits a longitudinal section which is similar to a venturi tube and the hole 8 is arranged at the smallest-section end, i.e. the gullet end. The medicinal mixture which drops down from the capsule 30 is very effectively drawn into the air flow in transit towards the mouth of the user, and the depression which is created in the gullet section of the conduit 3 draws any residues of medicinal mixture left in the capsule 30 or the hole 8 into the conduit 3. To prevent blockage, the hole 8 internally comprises a baffle 9 arranged across a diameter of the hole 8.

The second body 4 comprises a seating 15 which faces onto the second surface 14 and is predisposed to be inserted on the pivot 12 and to achieve a rotatable coupling between the main body 2 and the second body 4, in which coupling the first surface 10 and the second surface 14 are in reciprocal contact, one sliding on the other. The seating 15 is afforded in the breadth of the second body 4 and is oriented so that a lateral surface thereof is arranged perpendicular to the second surface 14. In the illustrated embodiment, the seating 15 exhibits a C-shaped transversal section and the pivot 12 has a cylindrical shape with a lateral flat area enabling the main body 2 and the second body 4 to be unhinged in a predetermined angular position.

The second body 4 further exhibits a ledge 16 made along an edge of the second body 4, a shape of which complements the undercut 13a of the guide spur 13 and which is predisposed to interact in contact with the undercut 13a. When the main body 2 and the second body 4 are coupled, the ledge 16 is inserted below the undercut 13a and rotations that tend to separate the first surface 10 and second surface 14 are prevented.

The second body 14 further comprises a strike surface 17, perpendicular to the longitudinal development of the ledge 16, arranged at an end of the ledge 16 itself, and predisposed to meet the strike surface 13b of the guide spur 13. The contact between the strike surface 17 and the strike surface 13b defines a limit to angular displacement between the first surface 10 and the second surface 14, which limit is the closed position.

To ease opening and closing of the inhalator, the second body 4 comprises a transversal maneuvering surface 18, perpendicular to the second surface 14 and extending on the opposite side of the second body 4 with respect to the second surface 14. By acting on the maneuvering surface 18 it is extremely simple to perform a cutting action on a capsule 30 inserted in the housing 5.

The inhalator of the invention offers important advantages.

First of all, it basically comprises only two components, assembly of which is extremely simple. The inhalator is thus decidedly economical to produce and is practically without risk of jamming or malfunctioning.

Secondly, the arrangement of the housing for the capsule, as well as the complete cutting-open thereof, make the contents of the capsule fully available for inhalation, giving the user the certainty of having completely inhaled the correct dose. If transparent materials have been used, the user can fully check, even more easily, that he or she has completed inhalation of the full dose.

Thirdly, as the medicinal mixture is deposited internally of the inhalation conduit and internally of the flow of air created by the user's aspiration, the inhalator can be kept in a horizontal position. In this horizontal position, the longitudinal axis of the inhalation conduit is aligned with the mouth of the user, which enables the medicinal powders to reach the trachea without depositing on the internal parts of the mouth.

What is claimed is:

1. An inhalator for single-dose mixtures in capsules comprising a main body having an inhalation conduit, wherein the main body comprises a first surface which extends planar and parallel to a longitudinal axis of the inhalation conduit and exhibits a hole for communication with the inhalation conduit; the inhalator also comprises a second body which exhibits a second surface, shaped complementarily to the first surface and placed in contact with the first surface, on which first surface a housing is fashioned, into which housing a capsule can be at least partially inserted; the second body being rotatably coupled with the main body, and being able to rotate from an open position, in which the housing is accessible from outside for insertion of a capsule, and a closed position, in which the housing is aligned with the hole; the inhalator also comprises cutting means for cutting off a portion of a capsule which projects from the housing during rotation of the second body from the open position to the closed position, said means for cutting comprising a cutting edge arranged peripherally on the first surface, a cut portion of said capsule remaining external of the inhalator.

2. The inhalator of claim 1, wherein the first surface exhibits an overall shape which is a segment of a circle, with an apex thereof located in an intermediate position with respect to a longitudinal development of the inhalation conduit and comprises a pivot which is perpendicular to the first surface and arranged at the apex of the first surface, and a guide spur which is perpendicular to the first surface and arranged along an arced edge of the first surface, the guide spur having an undercut and a strike surface.

3. The inhalator of claim 2, wherein the means for cutting comprise a cutting edge, arranged peripherally on the first surface and having a sawtooth profile.

4. The inhalator of claim 3, wherein the inhalation conduit exhibits a first mouth for aspiration of air from an outside environment, which first mouth is arranged on the first surface, and a second mouth for inhalation of a single-dose medicinal mixture, the hole being arranged on the first surface in an intermediate position between the first mouth and the second mouth.

5. The inhalator of claim 4, wherein the inhalation conduit exhibits a longitudinal section which is essentially a venturi tube, the hole being arranged in a narrowed, gullet section thereof.

6. The inhalator of claim 5, wherein the hole internally comprises a baffle arranged across a diameter of the hole.

7. The inhalator of claim 6, wherein the second body comprises a seating which faces the second surface, which seating can be inserted on the pivot to realize a rotatable coupling between the main body and the second body in which the first surface and the second surface are in reciprocal contact and slide one upon another; a ledge, fashioned along an edge of the second body, which ledge is complementarily shaped with respect to the undercut of the guide spur and which ledge is predisposed to interact contactingly with the undercut; a ledge strike surface which is perpendicular to a longitudinal development of the ledge and which is arranged at an end of the ledge, the ledge strike surface being destined to strike against the strike surface situated on the guide spur; a transversal maneuvering surface, perpendicular to the second surface, which extends on an opposite side of the second body with respect to the second surface.

* * * * *